US00PP13564P3

(12) United States Plant Patent
Danziger

(10) Patent No.: US PP13,564 P3
(45) Date of Patent: Feb. 18, 2003

(54) GYPSOPHILA PLANT NAMED 'DANGYPFIRM'

(75) Inventor: Gabriel Danziger, Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 09/838,249

(22) Filed: Apr. 20, 2001

(65) Prior Publication Data

US 2002/0157159 P1 Oct. 24, 2002

(51) Int. Cl.[7] ..... A01H 5/00
(52) U.S. Cl. ..... Plt./354
(58) Field of Search ..... Plt./354

(56) References Cited

PUBLICATIONS

GTITM UPOVROM Citation for 'Dangypfirm' as per IL PBR 03129; Nov. 22, 1999.*

* cited by examiner

*Primary Examiner*—Kent L. Bell
(74) *Attorney, Agent, or Firm*—Foley & Lardner

(57) ABSTRACT

A new and distinct Gypsophila plant named 'Dangypfirm' characterized by having hundreds of semi to full double flowers per stem, flowers arranged in clusters with outstanding stability and open formation, easy handling, prolonged vase life of 10–12 days, year round growing season under regular cultural practices, and suitable for both indoor and outdoor cultivation.

2 Drawing Sheets

LATIN NAME OF THE GENUS AND SPECIES OF THE PLANT CLAIMED

*Gypsophila paniculata.*

VARIETY DENOMINATION

Dangypfirm.

BACKGROUND OF THE INVENTION

The present invention relates to a new and distinct cultivar of Gypsophila plant, botanically known as *Gypsophila paniculata*, hereinafter referred to by the cultivar name 'Dangypfirm'.

The new cultivar originated from a cross made in a controlled breeding program in Mishmar Hashiva, Israel in 1999. The female parent is *Gypsophila paniculata*, 'F. CV.-1087' (unpatented). The male parent is *Gypsophila paniculata*, 'F. CV.-16' (unpatented). 'Dangypfirm' was discovered and selected by the inventor, Gabriel Danziger, as a flowering plant within the progeny of the stated cross in a controlled environment in Mishmar Hashiva, Israel.

Asexual reproduction of the new cultivar was accomplished by removing cuttings from the original plant and was first performed in a controlled environment in Mishmar Hashiva, Israel in May, 1999, by the inventor and has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'Dangypfirm' which in combination distinguish this Gypsophila as a new and distinct cultivar:

1. Hundreds of semi to full double flowers per stem;

2. Flowers arranged in clusters with outstanding stability and open formation;

3. Easy handling;

4. Prolonged vase life of 10–12 days; and

5. Year round growing season under regular cultural practices, suitable for both indoor and outdoor cultivation.

'Dangypfirm' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Mishmar Hashive, Israel under conditions which closely approximate those generally used in commercial practice.

Of the many commercial cultivars known to the present inventor, the most similar in comparison to 'Dangypfirm' is the cultivar 'Tavor' (U.S. Plant Pat. No. 9,301). In comparison to 'Tavor', 'Dangypfirm' inflorescence formation is in clusters, has a very rigid stem stability, a smaller flower, and higher number of petals.

The following chart provides a comparison between 'Dangypfirm' and the parental cultivars:

| Characteristic | 'Dangypfirm' | Female parental cultivar 'F. CV.-1087' | Male parental cultivar 'F. CV.-16' |
|---|---|---|---|
| Inflorescence formation | Clusters | Conice | Clusters |
| Stem stability | Very rigid | Stable | Stable |
| Flower size | 7 mm | 11 mm | 7 mm |
| Flowering rate in winter | 13–14 weeks | 13–15 weeks | 11–12 weeks |

BRIEF DESCRIPTION OF THE DRAWINGS

The accompanying photographic drawings show the overall appearance of 'Dangypfirm' showing the colors as true as is reasonably possible to obtain in colored reproductions of this type.

The first drawing depicts a whole plant view of a flowering 'Dangypfirm' plant.

The second drawing depicts a close-up view of the inflorescence of 'Dangypfirm'.

DETAILED BOTANICAL DESCRIPTION

The following observations, measurements and values describe the new cultivar, 14 weeks from planting, as grown in Mishmar Hashiva, Israel under conditions which closely approximate those generally used in commercial practice. Color references are made to The Royal Horticultural Society Colour Chart (R.H.S.), except where general colors of ordinary significance are used.

Propagation: Vegetatively by cuttings of side shoots.

Plant: General Appearance and Form: Height: 90–100 cm. Width: 60–70 cm. Habit: Upright bush consisting of 6–8 flowering stems forming a rosette with an apical dominance. Form: Bush, upright. Flowering Response: Long day. Flowering Season: Year round when supplementary lighting provided; natural flowering when day length exceeds 12 hours Lastingness of the Individual Bloom: 8–10 days on the plant; 10–12 days for cut plants (prolonged vase life). Rooting: A rooting hormone is used to spur root production. Fragrance: Typical of Gypsophila.

Foliage:

*Overall shape of leaf.*—Lanceolate. Base: Ovate. Tip: Acuminate.

*Margin.*—Entire.

*Texture.*—Smooth.

*Main color of upper surface.*—Mature leaf: Yellow-green RHS 147 A. Immature leaf: Yellow-green RHS 147 A.

*Main color of lower surface: Mature leaf: Green RHS* 137 A. Immature leaf: Green RHS 137 A.

*Venation.*—None.

*Leaf size.*—Length: 9–10 cm. Width: 16–20 mm.

*Attachment.*—Sessile.

*Stipules.*—None.

Inflorescence:

*Natural flowering season.*—During long day conditions.

*Corolla.*—Form: Round. Shape: "Cap" shaped. Average Number: Hundreds per branch, thousands per plant. Diameter: 7–8 mm. Petal Size: 3 mm in length, 1 mm in width. Margin: Entire with emarginated tip. Petal Number: 55–65. Petal Shape: Spathulated with tip emarginated. Petal Markings: None. Dorsal Petals: Free. Lateral Petals: Free. Petal Color: White RHS 155 C (both surfaces). Sepal number 5. Sepal shape: Lanceolate. Sepal length: 2 mm. Sepal apex: Acute. Sepal margin: Entire. Sepal color: Yellow-green RHS 146 A (both surfaces).

*Stem.*—Average length: 90–100 cm. Average diameter: 4–5 cm. Color: Yellow-green RHS 144 A. Internode length: 8–9 cm.

*Bud.*—Response: Long day conditions. Color: Sepal bud green RHS 146A; petal bud white RHS 155A. Size before opening: 3 mm in diameter; 2 mm in length. Pedicel: Length: 10–12 mm. Diameter: 0.2 mm. Color: Green RHS 144 A.

Reproductive organs:

*Pistils.*—Approximately 2.

*Stamen.*—10.

*Seeds.*—None produced.

*Fruit.*—None produced.

*Anthers.*—Yellow white.

*Pollen.*—Yellow white.

*Stigma.*—2. Color: White.

Disease resistance: Unsusceptible to most pests and diseases common in commercial fields, under regular growing conditions.

I claim:

1. A new and distinct Gypsophila plant named 'Dangypfirm', substantially as illustrated and described herein.

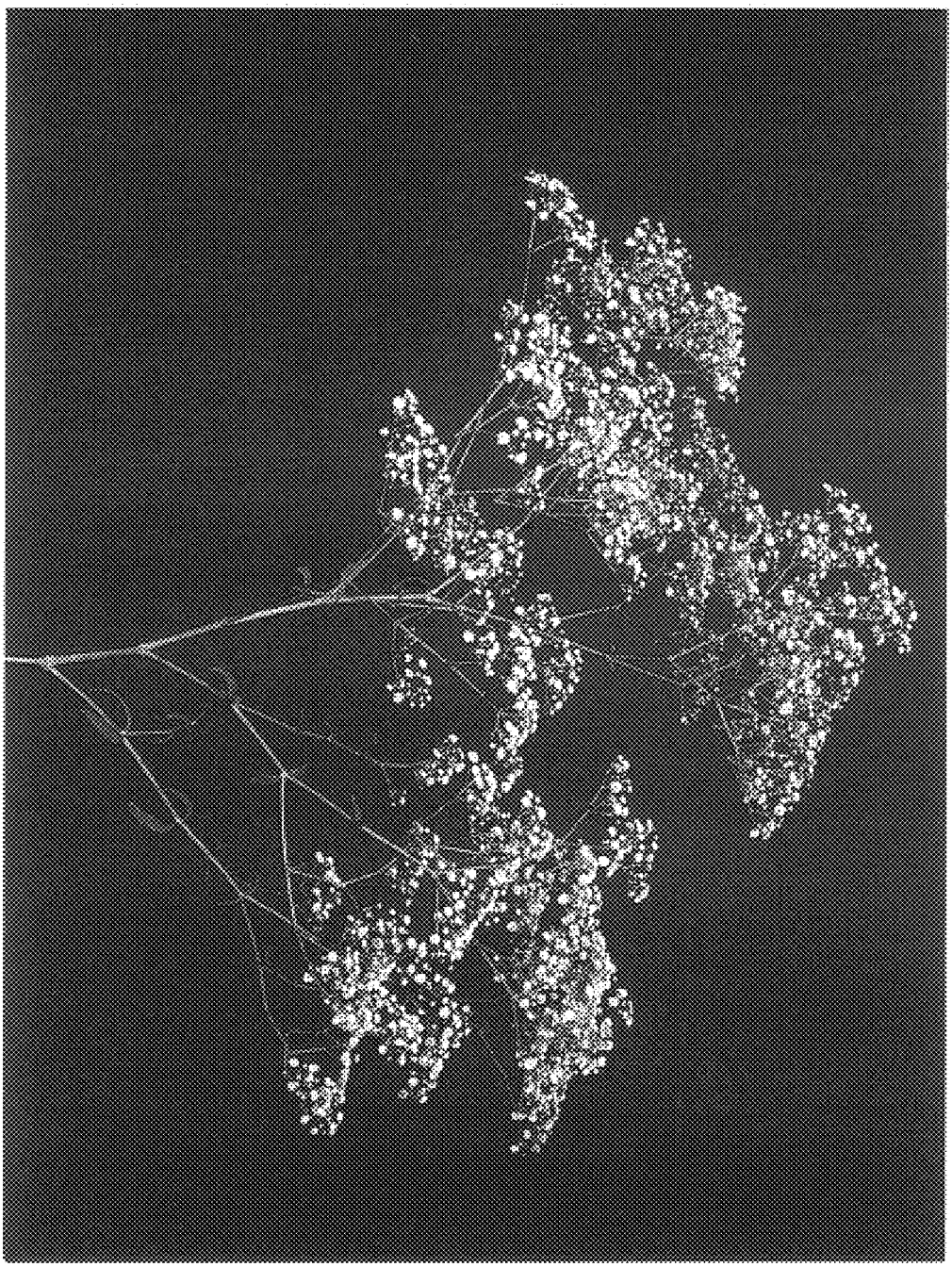

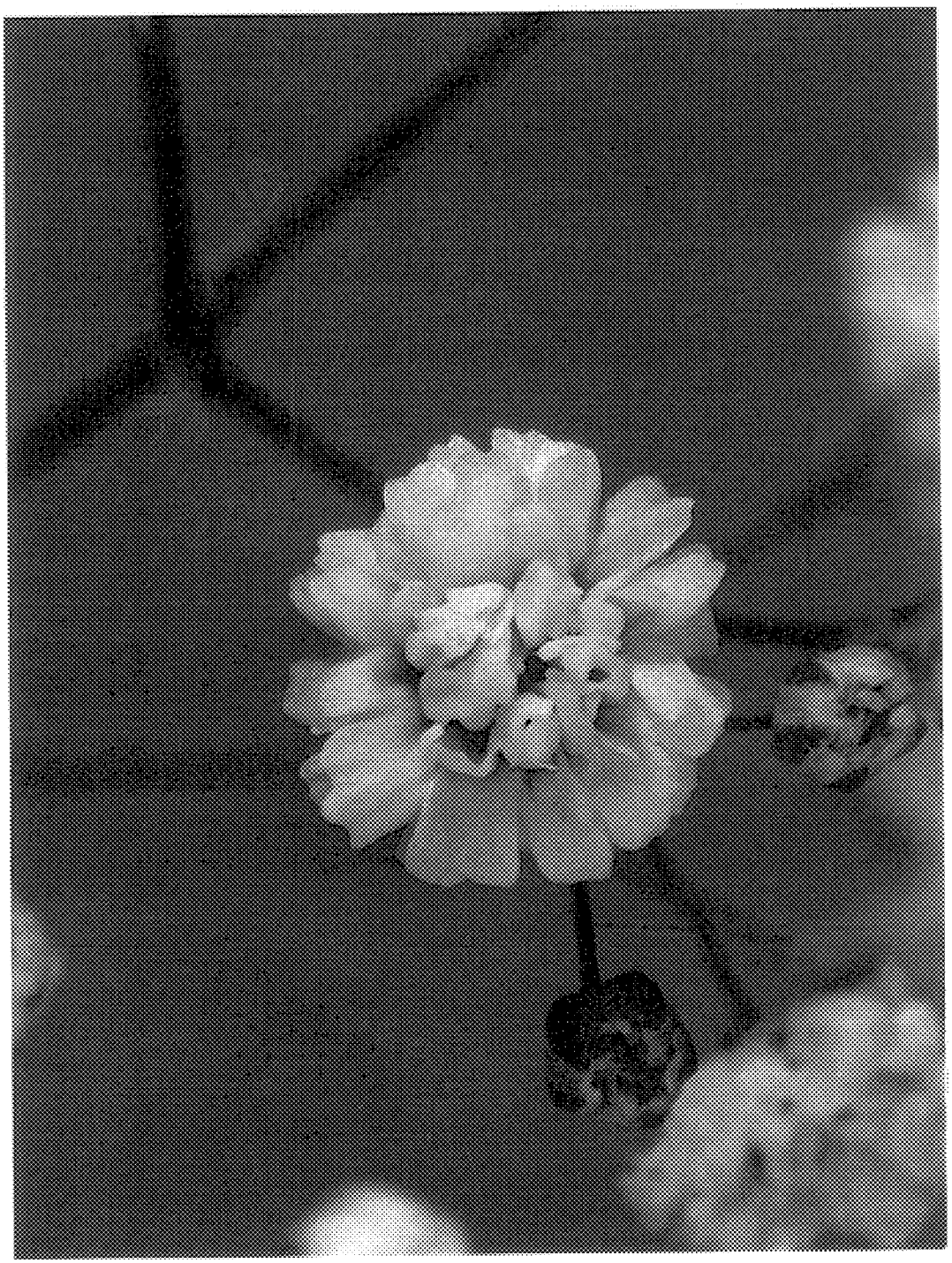

* * * * *